(12) United States Patent
Stehr et al.

(10) Patent No.: US 7,459,578 B2
(45) Date of Patent: Dec. 2, 2008

(54) PROCESS FOR THE PREPARATION OF ALK(EN)YLPHOSPHORIC ESTER SALTS

(75) Inventors: Wolfgang Stehr, Butzbach (DE); Matthias Loeffler, Niedemhausen (DE); Roman Morschhaeuser, Mainz (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 311 days.

(21) Appl. No.: 11/234,041

(22) Filed: Sep. 23, 2005

(65) Prior Publication Data

US 2006/0069278 A1 Mar. 30, 2006

(30) Foreign Application Priority Data

Sep. 24, 2004 (DE) .................. 10 2004 046 356

(51) Int. Cl.
*C07F 9/08* (2006.01)

(52) U.S. Cl. ...................................... 558/208

(58) Field of Classification Search ................. 558/208
See application file for complete search history.

(56) References Cited

U.S. PATENT DOCUMENTS

| | | | |
|---|---|---|---|
| 4,118,443 | A | 10/1978 | Klose |
| 6,066,753 | A | 5/2000 | Turowski-Wanke |
| 6,448,297 | B1 | 9/2002 | Turowski-Wanke |
| 6,803,478 | B2 | 10/2004 | Henning |
| 2003/0139622 | A1 | 7/2003 | Henning |

FOREIGN PATENT DOCUMENTS

| | | | |
|---|---|---|---|
| EP | 0 385 406 | A | 9/1990 |
| EP | 0 445 785 | A | 9/1991 |
| EP | 1120456 | | 8/2001 |
| EP | 1321470 | | 6/2003 |
| JP | 56-087589 | A2 | 7/1981 |
| JP | 62198690 | | 9/1987 |

OTHER PUBLICATIONS

Fukuda et al., 1988, CAS: 108:169703.*
English Language Abstract for JP62198690, Sep. 2, 1987.
English Language Abstract for EP1120456, Aug. 1, 2001.
Kasuga, K., et al., "Transport of Monosaccharides through a Liquid Membrane Mediated by Lipophilic Alkaline Earth Metal Complexes", Tetrahedron Letters, Elsevier, amsterdam, NL, vol. 39, No. 52, Dec. 24, 1998, pp. 9699-9702.
CAS Ascession No. 1982:34551, "Phosphoric Acid Monoester Salts", Jul. 16, 1981.
English Abstract for JP 56 087589.

* cited by examiner

*Primary Examiner*—Rei-tsang Shiao
(74) *Attorney, Agent, or Firm*—Tod A. Waldrop

(57) ABSTRACT

A process for the preparation of alk(en)ylphosphonc ester salts of the formula (I) and/or of the formula (II)

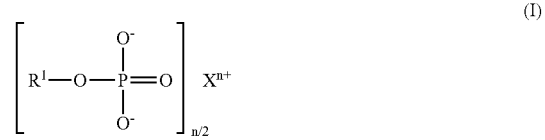

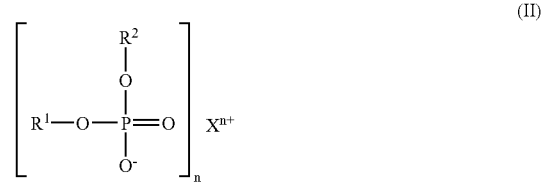

is described, in which $R^1$ and $R^2$ are identical or different and, independently of one another, are a linear or branched alkyl radical having 1 to 30 carbon atoms or are a linear or branched alkenyl radical having 2 to 30 carbon atoms and $X^{n+}$ is a cation with the valence n, which comprises reacting alk(en)ylphosphoric esters of the formula (III) and/or of the formula (IV)

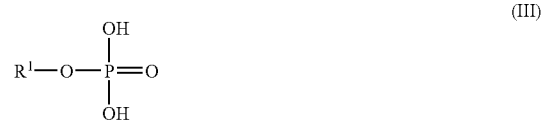

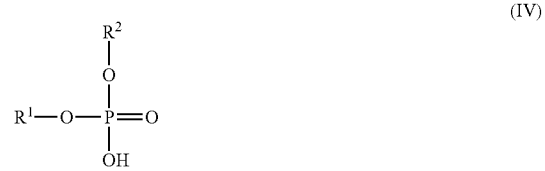

in which $R^1$ and $R^2$ have the meaning given above, in an aprotic solvent or aprotic solvent mixture with a base from which the cation $X^{n+}$ comes.

19 Claims, No Drawings

PROCESS FOR THE PREPARATION OF ALK(EN)YLPHOSPHORIC ESTER SALTS

The invention relates to a process for the preparation of alk(en)ylphosphoric ester salts from corresponding alk(en)ylphosphoric esters.

Alk(en)ylphosphoric esters are characterized by very good detergency properties and by high ecotoxicological compatibility. For this reason, these anionic surfactants are becoming increasingly important. Besides a use in liquid formulations, such as, for example, in hand dishwashing detergents and shampoos, the use of solid, solvent-free phosphoric esters, in particular salts thereof, in solid, anhydrous formulations is gaining importance. The phosphoric ester salts which, on account of their neutral pH values, are very well tolerated by the skin and are useful as emulsifiers in cosmetic and pharmaceutical formulations, but also in detergents and cleaners, are advantageous.

The preparation of alkyl and alkenylphosphoric esters is usually carried out by reacting tetraphosphorus decaoxide with fatty alcohols to form mono- and diesters with small fractions of triesters.

JP 62 198 690 describes a process for neutralizing phosphoric esters wherein the acidic phosphoric ester is dissolved in a hydroxyl-containing, water-soluble reaction medium, for example propylene glycol, and then a base is added. This process has the disadvantage that the hydroxyl-containing solvents themselves can undergo esterification reactions with the phosphoric ester, the product composition and thus the profile of properties is altered and the yield of the target product is reduced.

EP 1120 456 discloses the neutralization of phosphoric esters in an aqueous medium with subsequent drying in a fluidized bed. However, a high input of energy is required here.

EP 1 321 470 describes that the neutralization step of alk(en)ylphosphoric esters can be carried out without a solvent if a phosphoric ester, prepared by reacting tetraphosphorus decaoxide with fatty alcohol, is heated to melt and, with vigorous stirring, a hot saturated aqueous solution of neutralizing agent, for example alkali metal hydroxide, is metered in. Intensive mixing produces solid phosphoric ester salts. This process is unsatisfactory in that the phosphoric ester and neutralizing agent can only be thoroughly mixed with very complex and expensive kneader variants since the viscosity of the melt dramatically increases with increasing salt formation. Using customary paddle dryers, the mixing is only inadequate and the salt formation remains incomplete.

It was thus the object to develop a process for the preparation of solid, anhydrous salts of alk(en)ylphosphoric esters which is free from the disadvantages explained above.

Surprisingly, the object was achieved by reacting acidic alk(en)ylphosphoric esters in an aprotic solvent or aprotic solvent mixture with a base from which the counterion comes.

The invention thus provides a process for the preparation of alk(en)ylphosphoric ester salts of the formula (I) and/or of the formula (II)

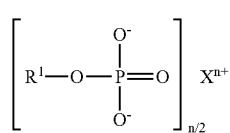
(I)

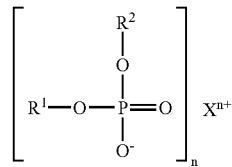
(II)

in which
$R^1$ and $R^2$ are identical or different and, independently of one another, are a linear or branched alkyl radical having 1 to 30 carbon atoms or are a linear or branched alkenyl radical having 2 to 30 carbon atoms and
$X^{n+}$ is a cation with the valence n, which comprises reacting alk(en)ylphosphoric esters of the formula (III) and/or of the formula (IV)

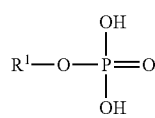
(III)

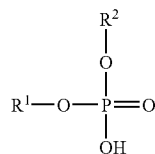
(IV)

in which
$R^1$ and $R^2$ have the meaning given above, in an aprotic solvent or aprotic solvent mixture with a base from which the cation $X^{n+}$ comes.

The process according to the invention is characterized, for example, by very high yields and a simple procedure.

The alk(en)ylphosphoric esters of the formulae (III) and (IV) are usually prepared by condensation of phosphorus pentoxide or orthophosphoric acid with alcohols, for example methanol, ethanol, propanol, isopropanol, butanol, in particular with fatty alcohols, such as caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol, brassidyl alcohol, and mixtures thereof.

During the preparation of the alk(en)ylphosphoric esters, mixtures of mono-, di- and triphosphoric esters regularly form whose pH is usually in the range 2 to 5.

In a preferred embodiment of the invention, the alk(en)ylphosphoric ester used is a mixture comprising alk(en)ylphosphoric esters of the formulae (III) and (IV), where the fraction of alk(en)ylphosphoric ester(s) of the formula (III), based on the mixture, is greater than 60% by weight and in particular is greater than 80% by weight. Fractions of triphosphoric esters are not troublesome during the reaction.

Preferably, the radicals $R^1$ and $R^2$ are identical or different and, independently of one another, are a linear or branched alkyl radical having 6 to 22 carbon atoms or are a linear or branched alkenyl radical having 6 to 22 carbon atoms.

It may be expressly noted that the term base also includes mixtures of chemically different bases. In this case, the alk(en)ylphosphoric ester salts of the formulae (I) and (II) regularly comprise different cations $X^{n+}$ which come from the different bases during the neutralization.

The bases may be all organic or inorganic bases which are suitable for neutralizing the OH groups of the alk(en)ylphosphoric esters.

The base is preferably used in the form of an aqueous solution or in the form of a powder. The base is particularly preferably used in the form of a concentrated aqueous solution, a saturated aqueous solution or in the form of a powder. The base is extraordinarily preferably used in the form of a saturated aqueous solution.

The bases are preferably chosen from metal hydroxides, metal oxides, ammonia, primary amines, secondary amines, tertiary amines, alkanolamines, amino acids and mixtures of these substances.

Accordingly, the cations $X^{n+}$ in the formulae (I) and (II) are preferably metal ions, $NH_4^+$ and ammonium ions derived from amines, alkanolamines and amino acids. Preferably, n has the value 1, 2 or 3, particularly preferably the value 1 or 2 and especially preferably the value 1.

Preferred metal hydroxides are alkali metal hydroxides, in particular NaOH and KOH, alkaline earth metal hydroxides, in particular $Ca(OH)_2$, and earth metal hydroxides, in particular $Al(OH)_3$.

Preferred amines are primary amines with long-chain alkyl groups having 1 to 30 carbon atoms, particularly preferably having 4 to 22 carbon atoms, or primary amines with aryl groups having 6 to 30 carbon atoms, particularly preferably having 6 to 10 carbon atoms.

Preferred alkanolamines are monoethanolamine, diethanolamine and triethanolamine.

Particularly preferred bases are chosen from alkali metal hydroxides, alkaline earth metal hydroxides and mixtures of these substances. The bases are particularly preferably chosen from NaOH, KOH, $Ca(OH)_2$ and mixtures of these substances, the base KOH being very particularly preferred.

The molar ratio of alk(en)ylphosphoric ester(s) to base is preferably in the range from 1:0.1 to 1:2, particularly preferably in the range from 1:0.75 to 1:1.25, especially preferably in the range from 1:0.9 to 1:1.1 and is very particularly preferably 1:1.

According to the invention, for the neutralization of the alk(en)ylphosphoric esters with bases, the phosphoric esters according to the formula III and/or IV are dissolved or suspended in aprotic solvents.

Preferably, the aprotic solvent or the aprotic solvent mixture is chosen from aliphatic hydrocarbons, cyclic hydrocarbons, aromatic solvents and mixtures of said solvents.

Preferred aliphatic hydrocarbons are chosen from straight-chain or branched $C_5$-$C_{30}$-alkanes and straight-chain or branched $C_5$-$C_{30}$-alkenes.

Preferred cyclic hydrocarbons are chosen from $C_5$-$C_8$-cycloalkanes.

Preferred aromatic solvents are chosen from aromatic hydrocarbons, in particular from benzene, toluene, ethylbenzene, xylenes and cresols. Of these aromatic solvents, preference is in turn given to toluene and xylenes.

The aprotic solvent or the aprotic solvent mixture is particularly preferably chosen from pentane, hexane, heptane, cyclohexane, toluene, xylenes and mixtures of these solvents.

The aprotic solvent cyclohexane is extraordinarily preferred.

In a preferred embodiment of the process according to the invention, the water of reaction is removed azeotropically.

The reaction of the alk(en)ylphosphoric esters with the base preferably takes place at temperatures of from 0 to 300° C. and particularly preferably at temperatures of from 25 to 180° C. and is carried out preferably over a period of from 0.1 to 10 hours, particularly preferably from 0.1 to 5 hours and especially preferably from 0.1 to 3 hours.

During the preparation of the alk(en)ylphosphoric ester salts of the formula (I) and/or of the formula (II), the procedure preferably involves dissolving or suspending the alk(en)ylphosphoric esters of the formula (III) and/or of the formula (IV) in an aprotic solvent or aprotic solvent mixture, heating the resulting solution or suspension to the boiling temperature, slowly metering in the base from which the cation $X^{n+}$ comes, removing the water of reaction azeotropically and distilling off the solvent or solvent mixture at reduced pressure.

Advantageously, the reaction temperature is in the region of the boiling point of the solvent used since the water of reaction which forms is entrained azeotropically at the boil. In the case of cyclohexane, the optimum operating tempreature is 80 to 87° C.

The product which forms is suitably formulated following cooling to room temperature. For example, the product can be bottled as block goods or be processed to give flake goods. It is preferably ground to a powder or to granules, preferably with particle sizes of from 0.1 μm to 1 cm.

The alk(en)ylphosphoric ester salts prepared according to the invention are suitable for use in cosmetic and pharmaceutical formulations, in particular for the preparation of oil-in-water emulsions, but also of water-in-oil emulsions, and likewise as detergents in washing and cleaning compositions, and as adjuvant in pesticides.

The alk(en)ylphosphoric ester salts are usually used in amounts of from 0.1 to 10% by weight, preferably from 0.3 to 4% by weight, based on the finished formulations.

Further auxiliaries and additives which may be present in the formulations are, inter alia, surfactants, emulsifiers, oil bodies, bleaches, superfatting agents, fats, waxes, stabilizers, biogenic active ingredients, glycerol, preservatives, dyes and/or fragrances.

The examples below serve to explain the invention in more detail but without limiting it thereto. All of the percentages given are percentages by weight.

General Process Procedure 800 g of Hostaphat® CC 100 were initially introduced into a 5000 ml paddle dryer and dissolved with 800 g of organic solvent. The solution was initially heated to boiling temperature and maintained at reflux. Then, in an equimolar amount, potassium hydroxide (as 50, 80 or 95% strength by weight aqueous solution) was metered in over the course of half an hour (½ h) and the water which formed was largely removed azeotropically. When the KOH addition was complete, the mixture was distilled off (solvent, water of reaction) under reduced pressure to product dryness and then cooled to 20° C. After-stirring was carried out for about 1 h and the product was then removed from the dryer and suitably formulated.

EXAMPLE 1

Preparation of the Potassium Salt of the Monophosphoric Ester with 50% Strength by Weight KOH in cyclohexane 1) Initial charge of 800 g of Hostaphat® CC 100 (monocetyl phosphate, Clariant) in the paddle dryer
2) Dissolution in 800 g of cyclohexane 3) Heating to boiling temperature (about 85° C.)
4) Addition of 306 g of KOH (50% strength by weight) over the course of 0.5 h at boiling temperature and azeotropic removal of water of reaction
5) Distilling off of solvent and residual water at 20 to 70° C. and 0.1 to 500 mbar
6) Cooling to 20° C. and stirring for about 1 h
7) Formulation by grinding.

EXAMPLE 2

Preparation of the potassium salt of the monocetyl phosphoric ester with 80% strength by weight KOH in cyclohexane 1) Initial charge of 800 g of Hostaphat® CC 100 (monocetyl phosphate, Clariant) in the paddle dryer
2) Dissolution of 800 g of cyclohexane
3) Heating to boiling temperature (85° C.)
4) Addition of 191 g of KOH (80% strength by weight) over the course of 0.5 h at boiling temperature and azeotropic removal of water of reaction
5) Distilling off of solvent and residual water at 50 to 70° C. and 2 to 500 mbar
6) Cooling to 20° C. and stirring for about 1 h
7) Formulation by grinding.

EXAMPLE 3

Preparation of the Potassium Salt of the Monocetyl Phosphoric Ester with 50% Strength by Weight KOH in n-hexane 1) Initial charge of 800 g of Hostaphat® CC 100 (monocetyl phosphate, Clariant) in the paddle dryer
2) Dissolution in 800 g of n-hexane
3) Heating to boiling temperature (about 80° C.)
4) Addition of 306 g of KOH (50% strength by weight) over the course of 0.5 h at boiling temperature and azeotropic removal of water of reaction
5) Distilling off of solvent and residual water at 20 to 80° C. and 10 to 900 mbar
6) Cooling to 20° C. and stirring for about 1 h
7) Formulation by grinding.

EXAMPLE 4

Preparation of the Potassium Salt of the Monocetyl Phosphoric Ester with 95% Strength by Weight KOH in n-hexane 1) Initial charge of 800 g of Hostaphat® CC 100 (monocetyl phosphate, Clariant) in the paddle dryer
2) Dissolution in 800 g of n-hexane
3) Heating to boiling temperature (about 80° C.)
4) Addition of 161 g of KOH (95% strength by weight) over the course of 0.5 h at boiling temperature and azeotropic removal of water of reaction
5) Distilling off of solvent and residual water at 20 to 70° C. and 100 to 900 mbar
6) Cooling to 20° C. and stirring for about 1 h
7) Formulation by grinding.

The product of examples 1 to 4 is a white to slightly yellowish powder with a melting point of from 150 to 170° C.

The invention claimed is:

1. A process for the preparation of an alk(en)ylphosphoric ester salt of the-formula (I) or of the formula (II) or mixtures thereof

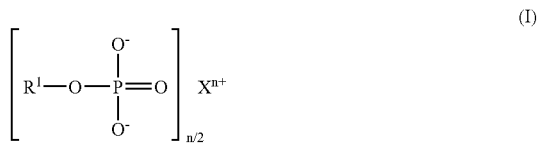

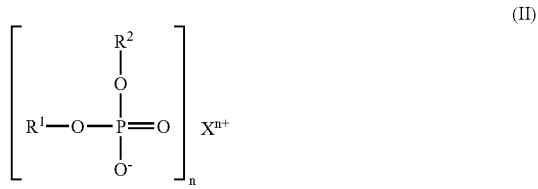

wherein
n is 1, 2, or 3,
$R^1$ and $R^2$ are identical or different and, independently of one another, are a linear or branched alkyl radical having 1 to 30 carbon atoms or are a linear or branched alkenyl radical having 2 to 30 carbon atoms and
$X^{n+}$ is a cation with the valence n,
comprising the step of reacting an alk(en)ylphosphoric ester of the formula (III) or of the formula (IV) or mixtures thereof

wherein
$R^1$ and $R^2$ have the meaning given above,
with a base in an aprotic solvent or aprotic solvent mixture,
  wherein the aprotic solvent or the aprotic solvent mixture is chosen from aliphatic hydrocarbons, cyclic hydrocarbons, aromatic solvents and mixtures of said solvents, and
  wherein the cation $X^{n+}$ comes from the base.

2. The process as claimed in claim 1, wherein the alk(en)ylphosphodc ester used is a mixture comprising alk(en)ylphosphoric esters of the formulae (III) and (IV), where the fraction of alk(en)ytphosphoric ester(s) of the formula (III), based on the mixture, is greater than 60% by weight.

3. The process as claimed in claim 1, wherein $R^1$ and $R^2$ are identical or different and, independently of one another, are a linear or branched alkyl radical having 6 to 22 carbon atoms or are a linear or branched alkenyl radical having 6 to 22 carbon atoms.

4. The process of claim 1, wherein the base is used in the form of a concentrated aqueous solution, a saturated aqueous solution, a powder, and mixtures thereof.

5. The process as claimed in claim 4, wherein the base is used in the form of a saturated aqueous solution.

6. The process of claim 1, wherein the base is selected from the group consisting of metal hydroxides, metal oxides, ammonia, primary amines, secondary amines, tertiary amines, alkanolamines, amino acids, and mixtures thereof.

7. The process as claimed in claim 6, wherein the base is selected from the group consisting of alkali metal hydroxides, alkaline earth metal hydroxides, and mixtures thereof.

8. The process as claimed in claim 7, wherein the base is selected from the group consisting of NaOH, KOH, $Ca(OH)_2$ and mixtures thereof.

9. The process of claim 1, wherein the molar ratio of alk(en)ylphosphoric ester(s) to base is in the range from 1:0.1 to 1:2.

10. The process as claimed in claim 1, wherein the aprotic solvent or the aprotic solvent mixture is selected from the group consisting of pentane, hexane, heptane, cyclohexane, toluene, xylenes, and mixtures thereof.

11. The process as claimed in claim 10, wherein the solvent is cyclohexane.

12. The process of claim 1, wherein the reaction of the alk(en)ylphosphoric esters with the base takes place at temperatures of from 0 to 300° C and is carried out over a period of from 0.1 to 10 hours.

13. The process of claim 1, further comprising azeotropically removing water of reaction.

14. The process of claim 2, wherein the fraction of alk(en)ylphosphoric ester(s) of the formula (III) is greater than 80 percent by weight.

15. The process of claim 7, wherein the base is KOH.

16. The process of claim 9, wherein the molar ratio ranges from 1:0.75 to 1:1.25.

17. The process of claim 9, wherein the molar ratio is 1:1.

18. The process of claim 12, wherein said reaction is carried out over a period of from 0.1 to 5 hours.

19. The process of claim 12, wherein said reaction takes place at temperatures of from 25 to 180° C.

* * * * *